US012035937B2

(12) United States Patent
Lenau et al.

(10) Patent No.: US 12,035,937 B2
(45) Date of Patent: Jul. 16, 2024

(54) NEEDLE AND A METHOD OF MAKING A NEEDLE

(71) Applicant: Danmarks Tekniske Universitet, Kongens Lyngby (DK)

(72) Inventors: Torben Lenau, Kongens Lyngby (DK); Tomas Benzon, Kongens Lyngby (DK)

(73) Assignee: Danmarks Tekniske Universitet, Kongens Lyngby (DK)

( * ) Notice: Subject to any disclaimer, the term of this patent is extended or adjusted under 35 U.S.C. 154(b) by 73 days.

(21) Appl. No.: 16/611,898

(22) PCT Filed: May 8, 2018

(86) PCT No.: PCT/EP2018/061913
§ 371 (c)(1),
(2) Date: Nov. 8, 2019

(87) PCT Pub. No.: WO2018/206598
PCT Pub. Date: Nov. 15, 2018

(65) Prior Publication Data
US 2021/0077145 A1     Mar. 18, 2021

(30) Foreign Application Priority Data
May 8, 2017   (EP) ..................... 17169973

(51) Int. Cl.
*A61B 17/34*        (2006.01)
*A61B 17/00*        (2006.01)
(52) U.S. Cl.
CPC ...... *A61B 17/34* (2013.01); *A61B 2017/0088* (2013.01); *A61B 2017/3409* (2013.01); *A61B 17/3417* (2013.01)

(58) Field of Classification Search
CPC ................ A61B 17/34; A61B 17/3417; A61B 2017/3454; A61B 2017/3401;
(Continued)

(56) References Cited

U.S. PATENT DOCUMENTS 2,989,053 A * 6/1961 Hamilton ............... A61M 5/162
                                                 D24/112
4,092,138 A * 5/1978 Beitner ................... F25B 21/02
                                                 433/32
(Continued)

FOREIGN PATENT DOCUMENTS

JP            57120905         1/1981
WO           WO9900155         1/1999
(Continued)

*Primary Examiner* — Darwin P Erezo
*Assistant Examiner* — Brigid K Byrd
(74) *Attorney, Agent, or Firm* — McHale & Slavin, P.A.

(57) ABSTRACT

The invention relates to a polymer needle comprising a body portion with a cylindrical cross-section and a tip portion in extension to the body portion. The tip portion of the needle forms at least two converging surfaces defining an edge. The needle forms a plurality of conduits arranged about a central solid core. The conduits and the core extend from the body portion into the tip portion such that each conduit terminates in one of the tip surfaces and the solid core forms the tip. The invention further relates to an apparatus for cleaving a polymer fibre at elevated temperatures. The polymer needle is prepared by this cleaving apparatus. The cleaving apparatus comprises a holding means for holding the fibre, a guide for guiding the movement of a cleaving knife, and a cleaving knife forming a cutting face of V-shape.

18 Claims, 10 Drawing Sheets

(58) Field of Classification Search
CPC ........ A61B 5/150396; A61B 5/150427; A61B
5/150458; A61B 5/150374; A61B
5/150381; A61B 5/150442; A61M
5/3286; A61M 5/32; A61M 5/158; A61M
5/1582; A61M 5/3291; B21G 1/08
See application file for complete search history.

(56) References Cited

U.S. PATENT DOCUMENTS

| | | | | |
|---|---|---|---|---|
| 5,437,282 | A | * | 8/1995 | Koger ............... A61M 25/0045 600/463 |
| 5,478,328 | A | * | 12/1995 | Silverman ............... A61M 5/32 604/110 |
| 5,562,696 | A | * | 10/1996 | Nobles ................... A61B 1/042 600/101 |
| 5,607,401 | A | * | 3/1997 | Humphrey .......... A61M 5/3243 604/239 |
| 5,634,913 | A | * | 6/1997 | Stinger ................ A61M 25/06 604/272 |
| 6,302,875 | B1 | * | 10/2001 | Makower ................ A61B 8/12 604/528 |
| 2002/0024110 | A1 | * | 2/2002 | Iwatsu ................... H01L 21/563 257/E21.511 |
| 2008/0308523 | A1 | | 12/2008 | Krulevitch et al. |
| 2009/0099535 | A1 | * | 4/2009 | Wang .................. A61M 5/3291 72/368 |
| 2010/0239221 | A1 | | 9/2010 | Robichaud et al. |
| 2010/0298736 | A1 | * | 11/2010 | Levy .................. A61B 10/0283 600/566 |
| 2012/0078224 | A1 | | 3/2012 | Lerner et al. |
| 2014/0031758 | A1 | * | 1/2014 | Lee ...................... A61M 5/3286 604/189 |
| 2014/0052067 | A1 | * | 2/2014 | Sausse .............. A61M 37/0015 604/173 |
| 2014/0121538 | A1 | | 5/2014 | Hendriks et al. |
| 2014/0277052 | A1 | * | 9/2014 | Haseby ................ A61M 25/06 606/185 |
| 2016/0262795 | A1 | * | 9/2016 | Urbanski ............... A61M 5/007 |
| 2016/0338734 | A1 | * | 11/2016 | Shah .................. A61B 5/14503 |
| 2018/0256200 | A1 | * | 9/2018 | Benning ........... A61B 18/1492 |

FOREIGN PATENT DOCUMENTS

| WO | WO0170114 | 9/2001 |
|---|---|---|
| WO | WO03047669 | 6/2003 |
| WO | WO2005028019 | 3/2005 |
| WO | WO2006136062 | 12/2006 |
| WO | WO2007059005 | 5/2007 |
| WO | WO2008074065 | 6/2008 |
| WO | WO2009083651 | 7/2009 |
| WO | WO2010071939 | 7/2010 |
| WO | WO2011113865 | 9/2011 |
| WO | WO2013036992 | 3/2013 |
| WO | WO2013058879 | 4/2013 |
| WO | WO2018206598 | 11/2018 |

* cited by examiner

NEEDLE AND A METHOD OF MAKING A NEEDLE

CROSS REFERENCE TO RELATED APPLICATIONS

This is a national stage filing in accordance with 35 U.S.C. § 371 of PCT/EP2018/061913, filed May 8, 2018, which claims the benefit of the priority of European Patent Application No. 17169973.9, filed May 8, 2017, the contents of each are incorporated herein by reference.

FIELD OF THE INVENTION

The present invention relates to a needle and a method of making a needle.

BACKGROUND OF THE INVENTION

Needles are often made from ceramic material or steel. Ceramic needles are fragile and easily breakable. Steel needles are not fragile but they are more rigid and difficult to bend. Needles are typically used for delivering only one type of fluid at the time. On the other hand, there is a need to mix two or more reactive compounds at the latest possible time before application. In biomedicine, it could be cancer treatment or insulin delivery where fast and slow insulin are mixed. In electronics, it could be conductive liquids for soldering or reactive glue like epoxy. Polymer needles can be long and slender, and they are typically robust. Further, polymer needles exist with more than one fluid channel.

DESCRIPTION OF THE INVENTION

It is an object of embodiments of the invention to provide a needle with a central tip which can penetrate tissue and skin without being bended. It is a further object to provide a needle having sufficient longitudinal strength to enable penetration of inter alia skin and tissue, and yet sufficient sideway flexibility, i.e. flexibility allowing bending. The sideways flexibility may improve the compliance of the needle which is an advantage, e.g. if the needle is to remain inserted in the body of a patient.

It may be seen as a further object of embodiments of the invention to provide a method of manufacturing needles and which is cost effective.

The above-mentioned objects are complied with by providing, in a first aspect, a needle extending in an axial direction between an end and a tip and forming a body portion and a tip portion between the end and the tip, the body portion located between the tip portion and the end and having a cylindrical cross-section and the tip portion located between the body portion and the tip and forming at least two surfaces converging towards the tip and defining a cutting edge, the needle comprising a solid core and a peripheral portion extending about the core, the needle forming at least one conduit extending in the peripheral portion in the axial direction from the body portion into the tip portion where it terminates in one of the converging surfaces, and the core extending from the body portion into the tip portion where it forms the tip, wherein the core is made from a first material and the peripheral portion is made from a second material different from the first material, and wherein the converging surfaces extend continuously across an intersection between the core and the peripheral portion such that the cutting edge is defined both by first material and by the second material.

In the present context, the term "needle" refers to an element which may penetrate, for example, a patient's skin, any kind of tissue, or which may penetrate other matter, e.g., to serve as a dispenser in the electronic industry.

The needle may be a polymer needle, which herein means that at least part of the needle in which the conduits extend, i.e. the peripheral portion, is made from a polymer material. The polymer material may comprise polystyrene, polycarbonate, polyurethane and polyacrylate. The polymer material may also be TOPAS, Liquid Crystal Polymer (LCP), particle reinforced polymers, and similar. A needle made of a polymer material may have sufficient stiffness needed for insertion and manipulation inside a patient's skin or lymph nodes but at the same time, it may be sufficiently soft and non-fragile to avoid that it breaks. A polymer material may fulfil requirements with regard to stiffness. Furthermore, a polymer material may provide a needle which has a sideway flexibility which may be important for protecting tissue if the needle is bended unintendedly. Polymer needles are moderately stiff and can therefore resist bending to a certain extent. Polymer can be used in magnetic resonance (MR) scanning. If applied in the electronic industry, a polymer needle can provide safe use as polymer is an electrical insulator. A polymer needle may e.g. be suitable for dispensing electrically conducting liquids, such as soldering paste and conductive epoxies. Polymer materials are often low cost and easily destructible, and therefore needles made of polymer can be cheap and easily disposable.

The needle has a body portion with a cylindrical cross-section. The cylindrical cross-section is convenient for penetration into tissue. Furthermore, in one embodiment, the cylindrical cross section provides equal support in all directions, i.e., the needle will not have a preferred direction of bending.

A tip portion forms an extension of the body portion of the needle. The tip portion forms at least two converging surfaces defining a cutting edge. The body portion and the tip portion may be made as two separate parts which are joined, or they may be made in one piece. Due to the converging surfaces in the tip portion, the tip portion may have a different shape compared to the body portion.

The tip portion could be made by reshaping an elongated body which has the structure of the body portion. In that way, the non-reshaped part of the elongated body forms the body portion and the reshaped part forms the tip portion.

During insertion of the needle, e.g. in tissue, the tip and the tip portion penetrate the tissue. The term "cutting edge" is to be understood as an edge formed in the transition where the surfaces intersect and being suitable for cutting through a skin and/or tissue, e.g., an edge with a radius of curvature being at most 0.1 mm, or even at most 0.01 mm, or even at most 0.001 mm, or at least in the range of 0.005-0.2 mm, and/or in the range of 0.03-0.7 mm. The two converging surfaces may be either curved or plane, or alternatively one may be plane while another one may be curved.

The centre of the body portion is formed by a solid core which extends in an axial direction from the body portion into the tip portion where the core forms the tip. The core is solid and therefore provides a suitable structure for penetration of skin and tissue etc.

At least one conduit may extend in the peripheral portion which extends about the central solid core. The conduits are hollow channels extending in the axial direction through the body portion of the needle. The conduits may be used for fluid transport, for delivering e.g. medical substances, or for precise delivery of fluids like soldering solvent or conductive epoxies etc. in the electronic industry.

Multiple conduits may allow for injection of at least two different and possibly reactive liquids, as well as for making mixtures. Particularly, the conduits extend entirely embedded in the peripheral portion of the needle to thereby form completely closed conduits, e.g. only being open in the axial opposite tip portion and end of the needle.

The conduits and the core extend in the axial direction of the needle. They further continue into the tip portion of the needle. The conduits typically extend in the axial direction along a straight-line. Each conduit may extend in parallel with adjacent conduits through the body portion and into the tip portion, and the core is typically straight and extends in the axial direction, e.g. in parallel with conduits. With such a configuration, different fluids can travel from one end of the needle through the conduits, to the tip portion, without being mixed.

Within the present context, the tip portion is that end of the needle which is axially offset relative to the body portion and which has at least two converging surfaces. The tip is that part of the needle which terminates the needle, i.e. the tip portion is between the body portion and the tip of the needle. This terminology is for defining features of the invention and does not necessarily imply a structural transition between the tip portion and the tip.

Each conduit terminates in one of the at least two surfaces so that fluid can be delivered to its final destination.

The solid core forms the tip. As the solid core extends through the centre of the cylindrical body portion of the needle, the tip may be at the centre of the needle. Such a central tip may provide stability to the needle, especially during insertion, and it may prevent the needle from bending. Furthermore, the central tip of the needle may be much stronger than an oblique cut bevel shaped tip portion which is known from traditional needles made from metal or ceramic.

In one embodiment, the body portion may form an outer portion extending axially about the peripheral portion and forming an outer surface of the body portion. In this embodiment, the conduits may extend in the peripheral portion and they may thus be completely encapsulated in the peripheral portion, and be covered by the outer portion.

The outer portion may cover the peripheral portion partly or completely, and it could be made from a material having different properties than the material onto which it is applied.

The core of the needle is made from a first material and the peripheral portion is made from a second material different from the first material.

In one embodiment, the first material may have a higher E-module than the second material. The E-module defines the elastic modulus as a measure of the stiffness of a solid material and defines the relationship between stress (force per unit area) and strain (proportional deformation) in a material. The higher E-module supports the tip and facilitates the penetration e.g. into tissue etc.

In one embodiment, the first material may have a higher strength than the second material. The strength of material is the amount of force it can withstand and still recover its original shape. Again, the higher strength supports the tip and facilitates the penetration e.g. into tissue etc.

In one embodiment, the first material may have a higher geometric stiffness than the second material. The geometric stiffness depends on shape, e.g. the stiffness of an I-beam is much higher than that of a round tube made of the same material, thus having the same rigidity. Again, the higher stiffness supports the tip and facilitates the penetration e.g. into tissue etc.

In one embodiment, the first material may have a higher hardness than the second material. The hardness of a material defines the relative resistance that its surface imposes against the penetration of a harder body portion. Again, the higher hardness supports the tip and facilitates the penetration e.g. into tissue etc.

In one embodiment, the first material may have a higher toughness than the second material. The toughness is the amount of energy that a material can absorb before fracturing. Again, the higher toughness supports the tip and facilitates the penetration e.g. into tissue etc.

The outer portion could be made from a cover material having a higher E-module than the second material, and/or the cover may have a higher strength, geometric stiffness, hardness, and/or toughness than the second material.

The outer portion may be made from a cover material, the cover material having a higher E-module than the first material.

The outer portion could be made from a cover material having a lower E-module than the first material, and/or the cover may have a lower strength, geometric stiffness, hardness, and/or toughness than the first material In one embodiment, the outer portion may be made from a cover material, the cover material having a higher E-module than the first material. At least one of the first, second, and cover material could be a polymer material.

The first material may e.g. be a metal material such as e.g. a stainless steel alloy or titanium or an alloy containing titanium.

The cover material could be a ceramic material, or it could be a metal material such as e.g. a stainless steel alloy or titanium or an alloy containing titanium, or a combination between metal and ceramic, a combination between metal, ceramic and polymer, or a combination between ceramic and polymer material.

In one embodiment of the invention, the needle may be made from a drawn polymer fibre. Drawing of fibres is a well-known technology for the production of optical fibres. The polymer fibre used may be a hollow core fibre with multiple hollow cores. Hollow cores may represent conduits of the needle. The fibre may have one, two, three, or more internal conduits.

The conduits may extend along the body portion of the needle, all the way from the end to the tip portion so that fluid can be transported through the entire length of the needle. The conduits may have a circular cross-section, a rectangular, hexagonal, oval, or even an unregularly shaped cross-section. The shape of the conduits may depend on the fluid viscosity and the required fluid flow for a particular application. Furthermore, by choosing a shape other than circular, the cross-sectional area and thus the flow volume of a fluid may be maximized. The length of the conduits, i.e. the length of the needle may depend on the application of the needle. For instance, when applied for insertion in tissue, the length of the needle may be determined by the required penetration depth of tissue.

In one embodiment of the invention, the needle may comprise at least two conduits extending in the axial direction of the needle. The number of conduits depends on the application and required different number of fluids but 2, 3, 4, 5, 6 or even 7 or more conduits may be considered.

The conduits may remain separated throughout the needle from the end to the tip portion.

In one embodiment, the polymer needle may have the tip portion extending from the body portion such that the tip portion forms a plurality of surfaces. As mentioned above, the needle may comprise three conduits. In this case, the tip portion may form a 3-sided pyramid shape such that each of three conduits ends in one of the sides of the tip portion. Such a bevelled tip portion gives a balanced stress distribution eliminating high demands on the material stiffness to avoid buckling during insertion. Furthermore, the pyramid-shaped tip may have sharp edges in the intersection between the surfaces to thereby reduce resistance during insertion.

According to one of the embodiments of the invention, the tip portion of the needle may have bevel sides which make an angle in the range of 5°-45° with an axis extending along the axial direction. The tip may be designed to be inserted into a biological tissue and to introduce or remove a fluid to or from the biological tissue. The bevel sides may make an angle in the range such as 5°-35°, such as 5°-30°, such as 10°-25°, such as 15°-20°.

The angle of the bevel sides may depend on the application. Furthermore, there may be an optimal angle depending on the number of conduits so that the tip portion shows high stability.

In a yet another embodiment, the invention relates to a polymer needle which may have a tip portion extending from the body portion, the tip portion may have a conical shape. The needle with the conical tip portion may be produced using grinding. The conical shaped tip portion may also penetrate tissue efficiently. The tip of the cone may coincide with the central core of the needle. Having the tip of the needle coinciding with the centre of the body portion provides stability to the needle, particularly during insertion into tissue.

According to the invention, the polymer needle may have an outer diameter between 0.1 mm and 1 mm. The outer diameter of the needle may be in range such as between 0.2 mm and 0.9 mm, such as between 0.2 mm and 0.7 mm, such as 0.2 mm and 0.5 mm. Such a small diameter may be advantageous as thin needles can reach much deeper into tissue without damaging it. The number of conduits may be independent of the diameter of the needle. The flow resistance may increase for increasing number of conduits.

The tip portion of the needle may terminate in a sharp pointed tip which may facilitate penetration of tissue.

The tip portion of the needle may, alternatively, terminate in a tip formed by the cutting edge. In this embodiment, the cutting edge extends continuously, i.e. non-broken from one side of the tip, through the tip, to the other side of the tip.

In one embodiment of the invention, the needle may comprise a body portion with a cylindrical cross-section and a tip portion arranged in axial extension to the body portion, the tip portion terminating in a sharp pointed tip, wherein the needle forms at least one axially extending conduit being offset relative to an axially extending solid central core, each conduit and the core extending from the body portion into the tip portion such that each conduit terminates in a surface of the tip portion and the solid core forms the sharp pointed tip.

In a second aspect, the invention provides an apparatus for cleaving a polymer fibre at elevated temperatures, the apparatus comprising:
 a holding means for holding the fibre while the tip of the fibre is cleaved, the holding means forming a support for the fibre extending in an axial direction and at least partly enclosing the fibre, the support terminating in a working surface;
 a guide for guiding the movement of a cleaving knife at a predetermined angle relative to the axial direction; and
 a cleaving knife forming a guide surface configured to interact with the guide for moving the cleaving knife along the guide, the cleaving knife further forming a cutting face arranged to slide against the working surface during the movement of the cleaving knife along the guide, wherein the cutting face and working surface have a v-shape.

The cleaving apparatus is suitable for cutting any kind of fibres, such as silica fibres, polymer fibres, hollow-core fibres, photonic crystal fibres, and the like in a controlled manner in order to prepare a fibre for further use such as splicing, to decrease loss of the fibre end or to make a functional device from the cleaved fibre.

The term "elevated temperatures" is to be interpreted as temperatures higher than room temperature. However, the temperature may be lower than that temperature at which the polymer will melt. The temperature is elevated during the cleaving in order to reduce residual stress present in the fibre.

The cleaving apparatus comprises the holding means for holding the fibre during the cleaving. The holding means holds at least part of the fibre, namely one end of the fibre while another end, which will be cleaved, is free. The cross-section of the holding means may be rectangular, triangular, or any other shape having at least one flat surface so that it can be stable during the cleaving. The holding means forms a support for the fibre where the fibre is positioned. The support may be a conduit, a hole, a groove or the like. The size of the conduit may be at least as large as the diameter of the fibre. The holding means terminates in the working surface, i.e., the free end of the fibre which is not enclosed by the conduit may extend to the working surface. The holding means, as well as the entire cleaving apparatus may be made of aluminium, steel or similar.

In order to cleave the fibre, the fibre needs to be guided along a predetermined path so that correct interaction between the cutting knife and a fibre is ensured. This is performed by the guide. The guide may carry the holding means.

According to the invention, the cleaving knife has a cutting face, which is v-shaped. This shape allows a fibre to be cut along two sides in only one operational step.

According to one of the embodiments of the invention, the working surface is non-perpendicular to the axial direction. Typically, the working surface is angled compared to the guide.

The cleaving apparatus may be suitable for cleaving fibres of 0.1-1 mm in diameter. The outer diameter of the fibre may be in a range such as between 0.2 mm and 0.9 mm, such as between 0.2 mm and 0.7 mm, such as 0.2 mm and 0.5 mm. The fibre may have two or more internal hollow cores.

The v-shaped cleaving knife may be configured to simultaneously cleave two facets of a fibre. The first facet of a needle may be cut by another apparatus.

In a yet another embodiment of the invention, the cleaving knife is configured to create angled cuts of a fibre with respect to a longitudinal axis of the fibre.

In a third aspect, the invention relates to a polymer needle prepared with a cleaving apparatus described above, the needle having a body portion with a cylindrical cross-section and a tip portion in extension to the body portion, the tip portion forms at least two converging surfaces defining a cutting edge, wherein the needle forms a plurality of conduits arranged about a central solid core, the conduits and the core extending from the body portion into the tip portion such that each conduit terminates in one of the surfaces and the solid core forms the tip.

The fibre to be cut may be a hollow core fibre. The hollow cores of the fibre will play the role of the conduits once the needle is finalized. Having a fibre with three conduits arranged in a triangle allows for a three-sided pyramid shaped needle with a central tip. The cleaving apparatus is configured to cut one end of the fibre which forms the body portion of the needle, such that the tip portion of the needle is created.

The fibre may be coated with a cover material prior to the cleaving to provide a needle with cover material only on the un-cleaved body portion and with the tip portion being uncovered by the cover material. The cover material may have a higher E-module, a higher strength, geometric stiffness, hardness, and/or toughness than the material onto which it is applied. Additionally, the fibre may have a solid core made from a core material having a higher E-module, a higher strength, geometric stiffness, hardness, and/or toughness than the material surrounding the solid core.

In a fourth aspect, the invention relates to a method for manufacturing a polymer needle from a drawn fibre, the method comprising the steps of:

cleaving a single side of the needle; and placing the fibre in the apparatus for cleaving the fibre in which a v-shaped knife cleaves two sides of the fibre creating two other sides of the needle.

When manufacturing a polymer needle with a tip portion, the first step of cleaving a single bevelled side of a needle is straightforward as the tip can be supported during the cleaving step, viz. a single side of the tip portion is cleaved while the fibre is kept in place and orientation by the holding means. To cut the next two sides of the tip portion, a v-shaped cutting knife is used. The v-shaped knife combined with a tilted ramp ensures that the fibre is centred while the two faces are cut simultaneously. By performing these two steps, a sharp tip of a needle may be produced.

The fibre may be coated with a cover material prior to the cleaving to provide a needle with cover material only on the un-cleaved body portion and with the tip portion being uncovered by the cover material. The cover material may have a higher E-module, a higher strength, geometric stiffness, hardness, and/or toughness than the material onto which it is applied. Additionally, the fibre may have a solid core made from a core material having a higher E-module, a higher strength, geometric stiffness, hardness, and/or toughness than the material surrounding the solid core.

In a fifth aspect, the invention provides a method of administering a drug substance by use of a needle according to the first aspect of the invention. According to the method, the tip formed by the core is used for piercing skin and tissue of the subject and the conduit(s) are used for administering the drug substance while the needle is allowed to remain in the body and allowed to bend inside the body and thus follow the movement of the skin and tissue.

The cleaving apparatus of the second aspect, the needle produced by the cleaving apparatus of the third aspect of the invention, the method of manufacturing of the fourth aspect of the invention and the use of the needle for administering a drug substance according to the fifth aspect of the invention may include any of the features mentioned relative to the needle of the first aspect of the invention.

BRIEF DESCRIPTION OF THE DRAWINGS

The invention will now be described in further details with reference to the accompanying drawings, in which.

DETAILED DISCLOSURE OF THE INVENTION

In its most general aspect, the present invention relates to a polymer needle comprising a body portion with a cylindrical cross-section and a tip portion in extension to the body portion, the tip portion forming at least two converging surfaces defining a cutting edge, wherein the needle forms a plurality of conduits arranged about a central solid core, the conduits and the core extending from the body portion into the tip portion such that each conduit terminates in one of the surfaces in the tip portion and the solid core forms the tip.

Figure 1:
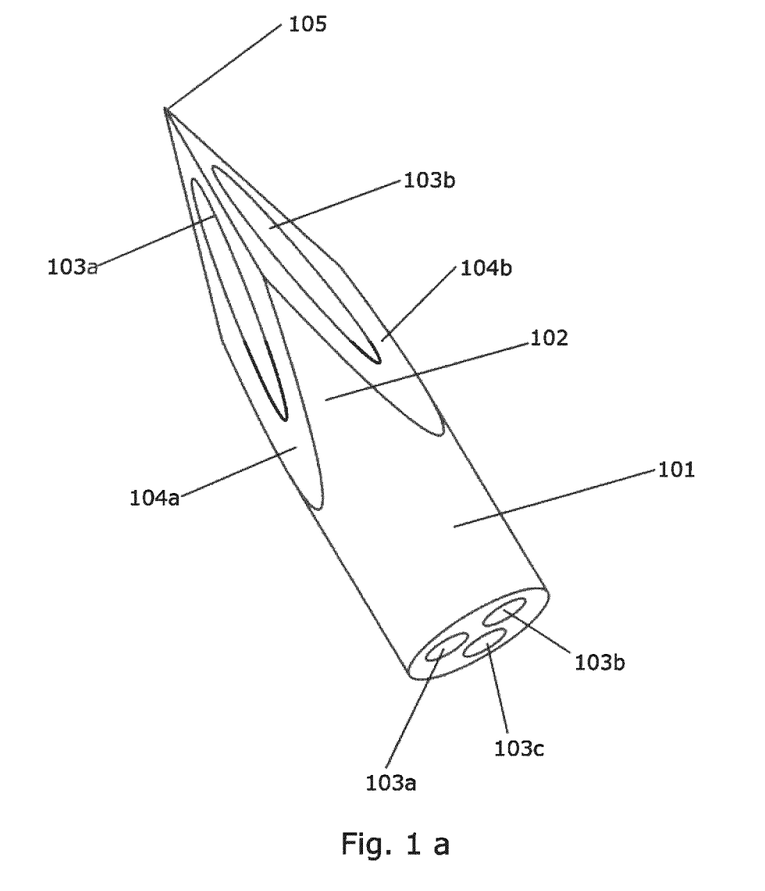
FIG. 1 illustrates a needle with three conduits and a central pyramid shaped tip portion.

FIG. 1a illustrates a polymer needle having a cylindrical body portion 101 and a pyramidal tip portion 102 extending from the body portion. The needle has three conduits 103a, 103b, and 103c extending along the needle. The three conduits terminate in three different surfaces of the tip portion. Only two conduits, 103a and 103b, and two surfaces, 104a and 104b, of the tip portion are shown in the tip surface. The pyramidal tip portion terminates with a sharp tip 105 which may efficiently penetrate tissue. FIG. 1b illustrates a circular cross-section of the needle. Three conduits, 103a, 103b, and 103c, are shown as well as a solid core 106. The solid core is in the centre of the circle and surrounded by the conduits which are arranged in a triangle. The solid core extends through the centre of the cylindrical body portion of the needle and forms the tip at the very end of the needle.

Figure 2:
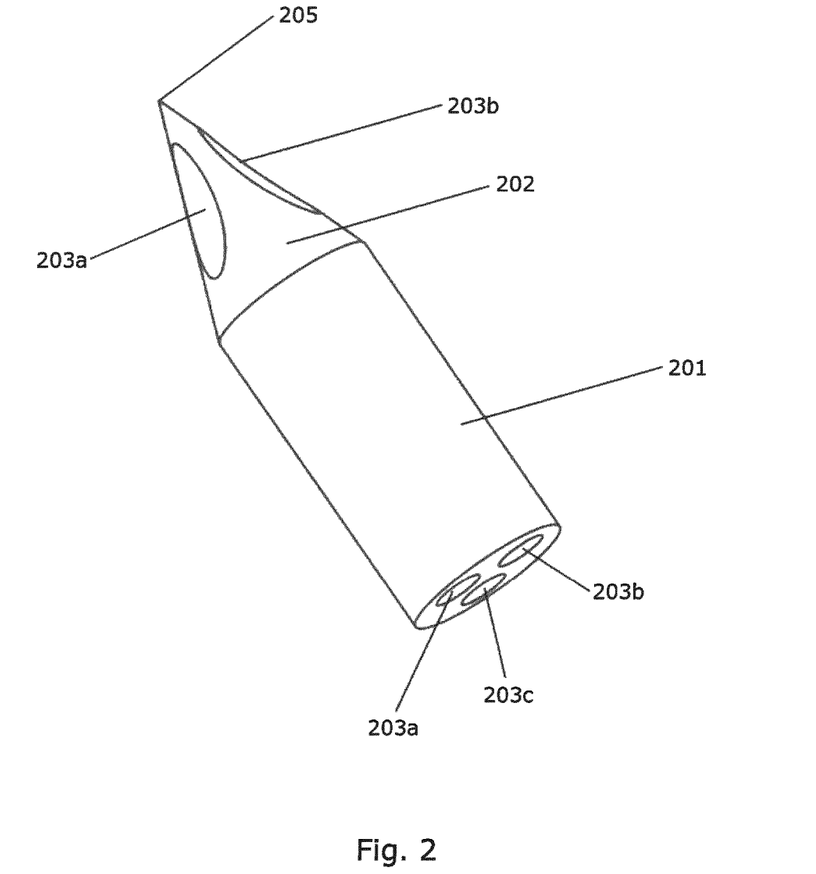
FIG. 2 illustrates a needle with three conduits and a conical tip portion.

FIG. 2 illustrates a polymer needle having a body portion 201 and a conical tip portion 202 extending from the body portion. The needle has three conduits 203a, 203b, and 203c extending along the needle and terminating in the tip surface. Only two conduits 203a and 203b are shown in the tip portion. The needle with the conical tip portion may be produced using grinding. The conical tip portion terminates with a sharp tip 205 which may also efficiently penetrate tissue.

Figure 3:
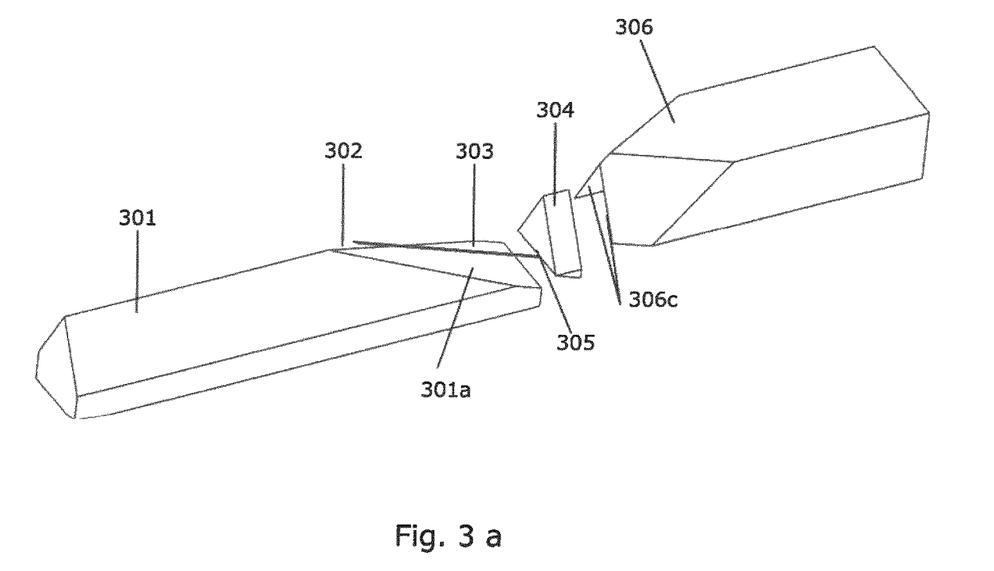
FIG. 3 illustrates a cleaving apparatus.

FIG. 3 illustrates a cleaving apparatus. FIG. 3a illustrates the apparatus in an exploded view, while FIG. 3b illustrates the apparatus in a position just before the knife cuts a fibre. In FIG. 3 all the elements of the apparatus are illustrated. These include: a guide 301, a support for a needle tip 302, a needle 303, a holder means which limits axial movements of a needle 304, a support 305 in the holder means 304 which positions and orientates a needle, and a v-shaped cleaving knife 306.

The holding means is arranged to hold the fibre while the tip of the fibre is cleaved, the holding means forming a conduit extending in an axial direction and at least partly enclosing the fibre, the conduit terminating in a working surface 301a. The guide 301 is configured to guide the movements of the cleaving knife 306 at a predetermined angle relative to the axial direction. The cleaving knife 306 forms a guide surface configured to interact with the guide 301 for moving the cleaving knife 306 along the guide 301. The cleaving knife 306 also forms a cutting face 306c arranged to slide against the working surface 301a and the tip support 302 during the movement of the cleaving knife along the guide. The cutting face 306c and working surface 301a have a v-shape.

FIG. 3c illustrates a zoomed-in view of the working surface 301a. It is shown that the working surface has an angled upper part 302 representing a support for a needle tip.

FIG. 3d illustrates a cross-section of two different exemplary embodiments of the holder means 304. The cross-section of the holder means are triangular, but may take another shape such as rectangular, hexagonal, or the like, with at least one flat surface. In one embodiment, the fibre/needle support 305 is a conduit while in another embodiment the support 305 is a groove. As mentioned earlier in the description, the support may take other shapes.

Figure 4:
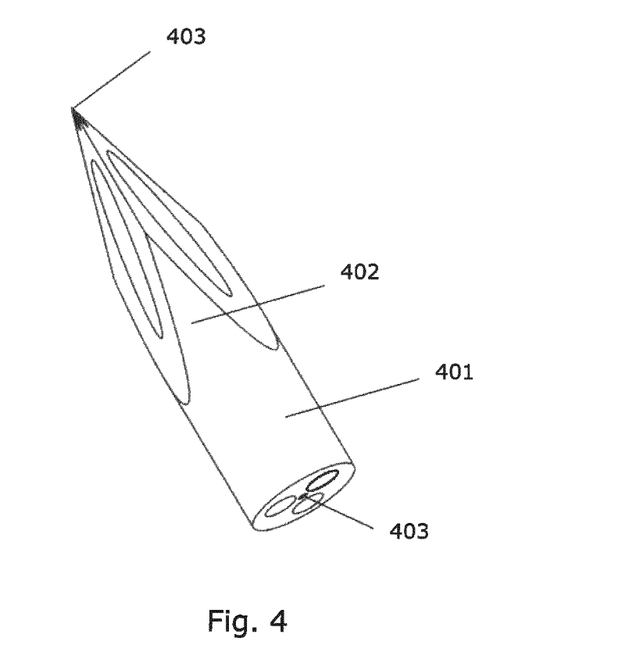
FIG. 4 illustrates a needle with a solid core and a peripheral portion.
Figure 5:
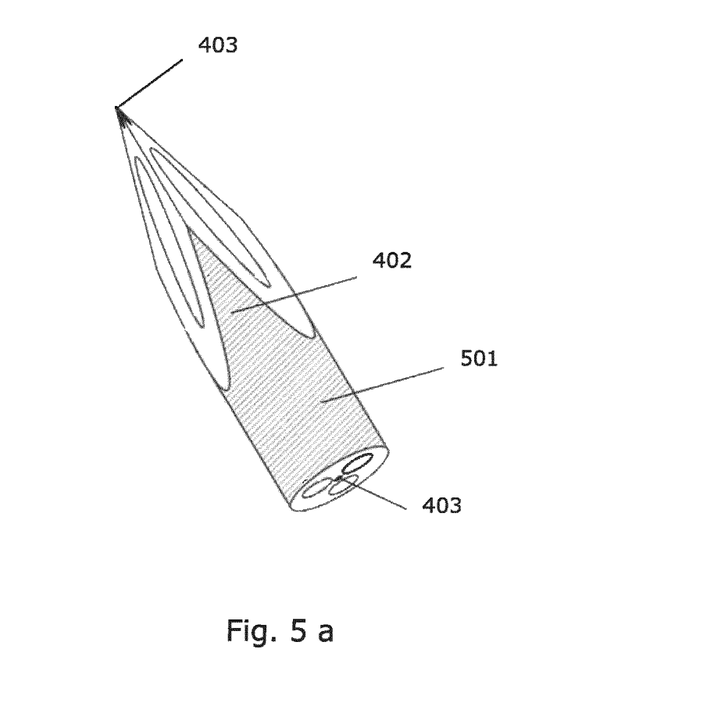
FIG. 5 illustrates a needle with a solid core, a peripheral portion and an outer portion.
Figure 6:
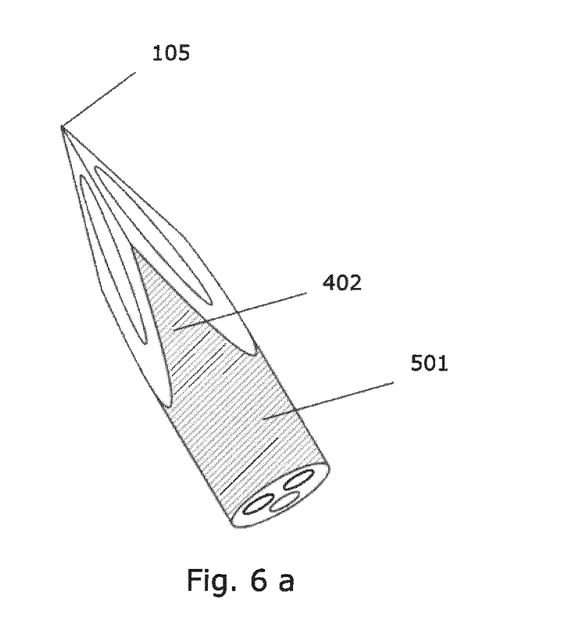
FIG. 6 illustrates a needle with an outer portion.

FIGS. 4-6 illustrate embodiments of the needle in which the solid core is made from a core material having different properties than the remaining part of the needle and/or in which the needle is covered partly or completely with a cover material having different properties than the material onto which it is applied.

In FIG. 4 the needle 401 has a solid core 403 and a peripheral portion 402. The solid core is made from steel, e.g. stainless medical grade steel or from titanium, and the peripheral portion is made from a polymer material. The tip portion terminates in a sharp pointed tip which is formed by the core. Due to the higher E-module of steel compared to the E-module of the polymer material, the tip becomes more durable and suitable for penetration through skin, tissue and similar matter. The lower E-module of the polymer increases the flexibility and enables easier bending into a desired shape. The three conduits extend entirely in the peripheral portion, i.e. in the polymer material, and the conduits are completely embedded in the peripheral portion to thereby form completely closed conduits only being open in the axial opposite ends.

FIG. 5a Illustrates the needle from FIG. 4 in an embodiment which further comprises an outer portion 501 extending axially about the peripheral portion and forming an outer surface of the body portion. The outer portion is made from a cover material, e.g. a ceramic material. The material may be applied in a vapour deposition process. In the disclosed embodiment, only the body portion is covered by the outer portion while the tip portion is un-covered. This can be obtained by covering the body portion prior to cleaving the tip portion. The material properties of the cover material may support the needle and prevent radial deformation.

FIG. 5b illustrates an alternative to the embodiment illustrated in FIG. 5a. In this embodiment, the tip portion is also covered by the outer layer. This embodiment can be obtained by applying the cover material to the needle after the tip production is finished, e.g. after cleaving etc. The cover material can be applied e.g. by vapour deposition.

FIG. 6a illustrates an embodiment of the needle with an outer portion 501 but in this embodiment, the solid core 105 is made from the same material as the peripheral portion 402, in this case a polymer material. The polymer used for the solid core 105 has different properties compared to the polymer used for the peripheral portion, such as a higher strength, geometric stiffness, hardness, and/or toughness. The body portion of the needle is covered by the outer portion 501, i.e. with a cover material having different properties than the polymer material of the solid core and peripheral portion. The tip portion is not covered by the cover material.

FIG. 6b illustrates the needle from FIG. 6a but with the tip portion also being covered by the cover material. In the illustrated embodiment, the entire tip portion is covered. Alternatively, only a part of the tip portion is covered by the cover material, e.g. the sharp pointed tip.

Figure 7:
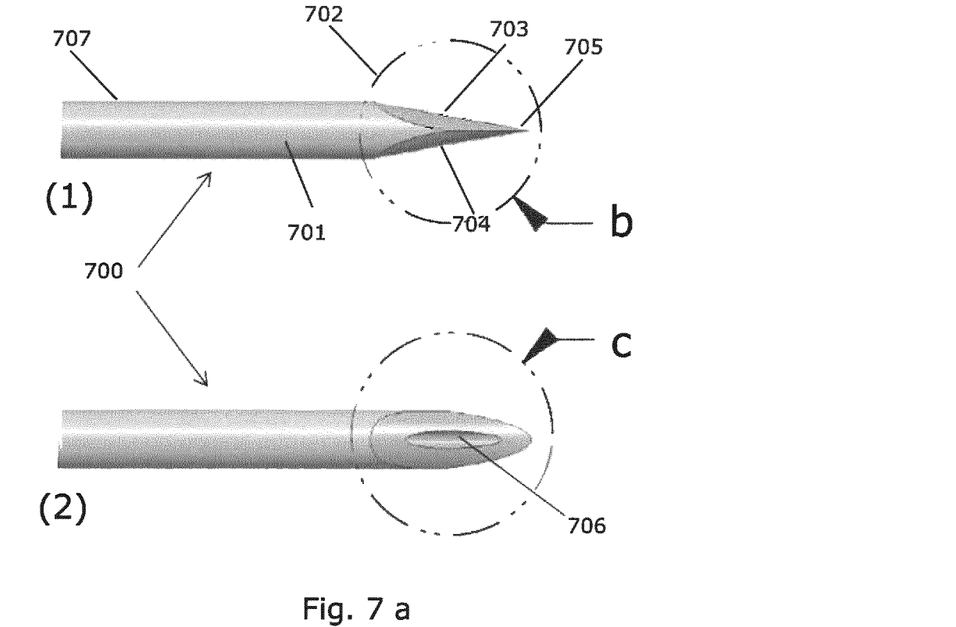
FIG. 7 illustrates a needle according to the first aspect of the invention.

FIG. 7a illustrates a part of a needle 700 seen from two different perspectives (1) and (2). The needle 700 comprises a body portion 701 with a cylindrical cross-section and a tip portion 702 arranged in axial extension to the body portion 701, wherein the tip portion 702 forms two converging surfaces 703 and 704 defining a cutting edge 705. The cutting edge 705 is defined along the intersection of the two converging surfaces.

The converging surfaces 703 and 704 are curved. The needle 700 forms two axially extending conduits 706 which are offset relative to an axially extending solid central core. Each conduit 706 and the core extend from the body portion 701 into the tip portion 702 such that each conduit 706 terminates in one of the two surfaces 703 and 705 of the tip portion 702. The body portion 701 forms a peripheral portion 707 extending about the solid core, and wherein the conduits 706 extend in the peripheral portion 707. The core is made from a first material and the peripheral portion 707 is made from a second material different from the first material. The converging surfaces 703 and 704 extend from the solid core into the peripheral portion 707.

FIG. 7b illustrates an enlarged view of the tip portion 702 seen from the perspective (1). The two converging surfaces 703 and 704 are clearly shown. FIG. 7c illustrates an enlarged view of the tip portion 702 seen from the perspective (2) clearly showing one of the conduits 706 terminating in one of the curved converging surfaces 704 (or 703). The cutting edge 705, i.e., the tip is also shown from two different perspectives (1) and (2).

FIG. 7d illustrates yet another enlarged view of the tip portion 702 of the needle 700. The solid central core 708 is visible from this perspective, illustrating that the conduits 706 are offset relative to the axially extending solid core 708. The core 708 forms the cutting edge 705.

FIG. 7e illustrates a cross-section of the needle 700 showing the two conduits 706, the solid central core 708, and the peripheral portion 707 where the core 708 is made from a first material and the peripheral portion 707 is made from a second material different from the first material.

FIG. 7f illustrates the tip of the needle and its enlarged view showing the cutting edge 705. The cutting edge 705 is an edge formed in the transition where the converging surfaces 703 and 704 intersect and is suitable for cutting through a skin and/or tissue, e.g., an edge with a radius of curvature R being at most 0.1 mm, or even at most 0.01 mm, or at least in the range of 0.01 to 0.2 mm, and/or in the range of 0.03 to 0.7 mm. The two converging surfaces 703 and 704 may be either curved or plane, or alternatively one may be plane while another one may be curved forming the edge suitable for cutting. The two converging surfaces 703 and 704 form an angle α which may be in the range between 15° and 60°, such as in the range between 35° and 55°.

It should be noted that the drawings are not to scale.

Examples

Solid polymer needles with conical tips sharpened using grinding have been successfully tested for insertion into lymph nodes which have been removed from rats and humans. The needles penetrated tissue without bending. Metabolic contrast liquid agents can be injected into the lymph nodes during magnetic resonance scanning. This makes it possible to study the cellular transformation of the flow of liquid contrast agent circulated in the tissue. This type of scanning of time dependent liquid flow in tissue requires that no metal is used. The time dependent scanning will be useful for the mapping of the inner morphological structure in other biological tissue and be an important supplement to traditional histology (microscopy of sliced tissue).

The cleaving apparatus described above has been used for producing polymer needles with pyramid shaped tips in three-step hot cleaving. The needles with conical tips have been produced using grinding.

Embodiments

1. A needle comprising a body portion with a cylindrical cross-section and a tip portion arranged in axial extension to the body portion, the tip portion terminating in a sharp pointed tip, wherein the needle forms at least one axially extending conduit being offset relative to an axially extending solid central solid core, each conduit and the core extending from the body portion into the tip portion such that each conduit terminates in a surface of the tip portion and the solid core forms the sharp pointed tip.

2. A needle according to embodiment 1, wherein the body portion forms a peripheral portion extending axially about the solid core and an outer portion extending axially about the peripheral portion and forming an outer surface of the body portion, and wherein the conduits extend in the peripheral portion.

3. A needle according to embodiment 2, wherein the core is made from a first material and the peripheral portion is made from a second material, the first material having a higher E-module than the second material.

4. A needle according to embodiment 3, wherein the outer portion is made from a cover material, the cover material having a higher E-module than the second material.

5. A needle according to embodiment 3 or 4, wherein the outer portion is made from a cover material, the cover material having a higher E-module than the first material.

6. A needle according to embodiment 3 or 4, wherein the outer portion is made from a cover material, the cover material having a lower E-module than the first material.

7. A needle according to embodiment 2, wherein the core and the peripheral portion are made uniformly from a third material and wherein the outer portion is made from a cover material, the cover material having a higher E-module than the third material.

8. A needle according to any of embodiments 3-7, wherein at least one of the first second, third, and cover material is a polymer material.

9. A needle according to any of embodiments 3-8, wherein the first material is a metal material.

10. A needle according to any of embodiments 4-9, wherein the cover material is a ceramic material.

11. A needle according to any of the preceding embodiments, comprising a plurality of conduits extending axially and concentrically about the core in the peripheral portion.

12. A needle according to embodiment 1, wherein needle is a polymer needle made exclusively of a polymer material.

13. A needle according to any of the preceding embodiments, wherein the needle is made from a drawn polymer fibre, the drawn fibre having two or more internal conduits.

14. A needle according to any of the preceding embodiments, wherein the tip portion forms a plurality of surfaces.

15. A needle according to any of the preceding embodiments, wherein the tip portion of the needle has bevel sides which make an angle in the range of 5°-45° with an axis extending along the axial direction.

16. A needle according to any of the preceding embodiments, the tip being designed to penetrate biological tissue and to introduce or remove a fluid to/from the biological tissue.

17. A needle according to any of the preceding embodiments, wherein the tip portion has a conical shape.

18. A needle according to any of the preceding embodiments, the needle having an outer diameter between 0.1 mm and 1 mm.

19. An apparatus for cleaving a polymer fibre at elevated temperatures, the apparatus comprising:
   a holding means for holding the fibre while the tip of the fibre is cleaved, the holding means forming a support extending in an axial direction and at least partly enclosing the fibre, the support terminating in a working surface;
   a guide for guiding movement of a cleaving knife at a predetermined angle relative to the axial direction; and
   a cleaving knife forming a guide surface configured to interact with the guide for moving the cleaving knife along the guide, the cleaving knife further forming a cutting face arranged to slide against the working surface during the movement of the cleaving knife along the guide, wherein the cutting face and working surface have a V-shape.

20. An apparatus according to embodiment 19, the apparatus being suitable for cleaving a fibre of 0.1-1 mm in diameter, the fibre having 2 or more internal channels.

21. An apparatus according to any of embodiments 19-20, wherein the v-shaped cleaving knife is configured to simultaneously cleave two facets of a fibre.

22. An apparatus according to embodiments 19-21, wherein the cleaving knife is configured to create angled cuts of a fibre with respect to a longitudinal axis of the fibre.

23. A needle prepared with an apparatus according to embodiments 19-22, the needle having a body portion with a cylindrical cross-section and a tip portion in extension to the body portion, the tip portion terminating in a sharp pointed tip, wherein the needle forms a plurality of conduits arranged about a central solid core, the conduits and the core extending from the body portion into the tip portion such that each conduit terminates in one of the surfaces and the solid core forms the tip. 24. A needle according to embodiment 23, wherein the surface by which each conduit terminate is a plane surface.

25. A method for manufacturing a needle from a drawn fibre, the method comprising the steps of:
   cleaving a single side of the needle; and
   placing the fibre in the apparatus for cleaving the fibre in which a v-shaped knife cleaves two sides of the fibre creating two other sides of the needle.

Further Embodiments

1. A polymer needle comprising a body portion with a cylindrical cross-section and a tip portion in extension to the body portion, the tip portion terminating in a sharp pointed tip, wherein the needle forms a plurality of conduits arranged about a central solid core, the conduits and the core extending from the body portion into the tip portion such that each conduit terminates in one of the tip surfaces and the solid core forms the tip.

2. A polymer needle according to embodiment 1, wherein the needle is made from a drawn polymer fibre, the fibre having two or more internal conduits.

3. A polymer needle according to embodiments 1 and 2, wherein the plurality of conduits are configured to transport fluid.

4. A polymer needle according to any of the preceding embodiments, wherein the needle comprises at least two conduits extending along the axial direction of the needle.

5. A polymer needle according to any of the preceding embodiments, wherein the tip portion of the needle is an extension to the plurality of conduits and therefore configured to transport fluid.

6. A polymer needle according to any of the preceding embodiments, wherein the tip portion extending from the body portion forms a plurality of surfaces.

7. A polymer needle according to any of the preceding embodiments, wherein the tip portion of the needle has bevel sides which make an angle in the range of 5°-45° with an axis extending along the axial direction, the tip being designed to be inserted into a biological tissue and to introduce or remove a fluid to/from the biological tissue.

8. A polymer needle according to embodiments 1-5, wherein the tip portion extending from the body portion has a conical shape.

9. A polymer needle according to any of the preceding embodiments, the needle having an outer diameter between 0.1 mm and 1 mm.

10. An apparatus for cleaving a polymer fibre at elevated temperatures, the apparatus comprising:
   a holding means for holding the fibre while the tip of the fibre is cleaved, the holding means forming a support extending in an axial direction and at least partly enclosing the fibre, the support terminating in a working surface;
   a guide for guiding movement of a cleaving knife at a predetermined angle relative to the axial direction; and
   a cleaving knife forming a guide surface configured to interact with the guide for moving the cleaving knife along the guide, the cleaving knife further forming a cutting face arranged to slide against the working surface during the movement of the cleaving knife along the guide, wherein the cutting face and working surface have a V-shape.

11. An apparatus according to embodiments 10 and 11, the apparatus being suitable for cleaving a fibre of 0.1-1 mm in diameter, the fibre having 2 or more internal channels.

12. An apparatus according to embodiments 10-12, wherein the v-shaped cleaving knife is configured to simultaneously cleave two facets of a fibre.

13. An apparatus according to embodiments 10-13, wherein the cleaving knife is configured to create angled cuts of a fibre with respect to a longitudinal axis of the fibre.

14. A polymer needle prepared with an apparatus according to embodiments 10-14, the needle having a body portion with a cylindrical cross-section and a tip portion in extension to the body portion, the tip portion terminating in a sharp pointed tip, wherein the needle forms a plurality of conduits arranged about a central solid core, the conduits and the core extending from the body portion into the tip portion such that each conduit terminates in one of the surfaces and the solid core forms the tip.

15. A method for manufacturing a polymer needle from a drawn fibre, the method comprising the steps of:
   cleaving a single side of the needle; and
   placing the fibre in the apparatus for cleaving the fibre in which a v-shaped knife cleaves two sides of the fibre creating two other sides of the needle.

The invention claimed is:

1. A needle extending in an axial direction between an end and a tip and forming a body portion and a tip portion between the end and the tip, the body portion located between the tip portion and the end and having a cylindrical cross-section and the tip portion located between the body portion and the tip and forming at least two surfaces converging towards the tip and where the at least two converging surfaces intersect defining a cutting edge extending from the tip towards the body portion, the needle comprising a solid core and a peripheral portion extending about the core, the needle forming at least one conduit extending in the peripheral portion in the axial direction from the body portion into the tip portion where the at least one conduit terminates in one of the at least two converging surfaces, away from the cutting edge, and the core extending from within the body portion into the tip portion where the core forms the tip, wherein the core is made from a first material and the peripheral portion is made from a second material different from the first material, and wherein the at least two converging surfaces extend continuously across an intersection between the core and the peripheral portion such that the cutting edge is defined by the first material and by the second material, each of the first and second material being exposed on the cutting edge, wherein the first material has a higher hardness than the second material, wherein the higher hardness supports the tip and facilitates the penetration into tissue.

2. The needle according to claim 1, wherein the body portion forms an outer portion extending about the peripheral portion and forming an outer surface of the needle.

3. The needle according to claim 2, wherein the first material has a higher E-module than the second material.

4. The needle according to claim 2, wherein the outer portion is made from a cover material, the cover material having a higher E-module than the second material.

5. The needle according to claim 2, wherein the outer portion is made from a cover material, the cover material having a higher E-module than the first material.

6. The needle according to claim 2, wherein the outer portion is made from a cover material, the cover material having a lower E-module than the first material.

7. The needle according to claim 2, wherein at least one of the first material, the second material, and a cover material is a polymer material.

8. The needle according to claim 2, wherein the first material is a metal material.

9. The needle according to claim 1, further including a cover material, wherein the cover material is a ceramic material.

10. The needle according to claim 1, wherein the at least one conduit comprises a plurality of conduits extending axially and being located concentrically about the core in the peripheral portion.

11. The needle according to claim 1, wherein the at least one conduit comprises a plurality of conduits extending axially in the peripheral portion.

12. The needle according to claim 11, wherein each conduit of the plurality of conduits forms an opening in a corresponding one of the at least two converging surfaces such that each surface of the at least two converging surfaces has one opening into the corresponding conduit.

13. The needle according to claim 1, wherein the first material and the second material are made of two different polymer materials.

14. The needle according to claim 1, wherein the at least two converging surfaces of the tip portion forms more than two converging surfaces.

15. The needle according to claim 1, wherein the at least two converging surfaces defines an angle in the range of 5°-45° to the axial direction.

16. The needle according to claim 1, wherein the tip portion terminates in a sharp pointed end.

17. The needle according to claim 1, wherein the cutting edge extends continuously across the tip from one side of the tip to the other side of the tip.

18. The needle according to claim 1, wherein the cutting edge has a radius of curvature of between 0.001 mm to 0.1 mm.

\* \* \* \* \*